United States Patent
Baulieu et al.

(10) Patent No.: US 8,034,798 B2
(45) Date of Patent: Oct. 11, 2011

(54) USE OF 3-METHOXY-PREGNENOLONE IN THE PRODUCTION OF A MEDICAMENT FOR TREATING NEURODEGENERATIVE DISEASES

(75) Inventors: Etienne-Emile Baulieu, Neuilly-sur-Seine (FR); Esther Fellous, Paris (FR); Paul Robel, Paris (FR)

(73) Assignee: MAPREG, Le Kremlin Bicetre (FR)

( * ) Notice: Subject to any disclaimer, the term of this patent is extended or adjusted under 35 U.S.C. 154(b) by 558 days.

(21) Appl. No.: 10/542,495

(22) PCT Filed: Jan. 16, 2004

(86) PCT No.: PCT/FR2004/000086
§ 371 (c)(1),
(2), (4) Date: Jan. 18, 2006

(87) PCT Pub. No.: WO2004/067010
PCT Pub. Date: Aug. 12, 2004

(65) Prior Publication Data
US 2006/0199790 A1    Sep. 7, 2006

(30) Foreign Application Priority Data
Jan. 17, 2003    (FR) ................................. 03 00507

(51) Int. Cl.
*A01N 45/00* (2006.01)
*A61K 31/56* (2006.01)
(52) U.S. Cl. .......................................... 514/169; 514/182
(58) Field of Classification Search .................. 514/169, 514/182
See application file for complete search history.

(56) References Cited

U.S. PATENT DOCUMENTS

| 6,245,757 B1* | 6/2001 | Chopp et al. | 514/177 |
| 2002/0072509 A1* | 6/2002 | Stein et al. | 514/169 |

FOREIGN PATENT DOCUMENTS

| EP | 1 310 258 A1 | 5/2003 |
| EP | 1310258 A1 * | 5/2003 |
| WO | WO 01/68068 A2 | 9/2001 |
| WO | WO 02/36128 A1 | 5/2002 |

OTHER PUBLICATIONS

MedlinePlus Medical Encyclopedia: Multiple Sclerosis, retrieved on Mar. 28, 2008 via www.nlm.nih.gov/medlineplus/ency/article/000737.htm, dated on Aug. 6, 2007, p. 1 and 2.*
MedlinePlus Medical Encyclopedia: Multiple Sclerosis, retrieved on Mar. 28, 2008, p. 2; also see WebMD: Multiple Sclerosis—Prevention, retrieved on Mar. 28, 2008 via www.webmd.com/multiple-sclerosis/tc/multiple-sclerosis-ms-prevention, dated on Mar. 23, 2006.*
The Merck Index (Twelfth Edition, 1996: p. 1328, compound 7915).*
Chemical Book (retrieved via www.chemicalbook.com for the structure of pregnenolone methyl ether), retrieved on Apr. 30, 2009.*
Merriam-Webster Online Dictionary: the Definition of Drug (www.merriam-webster.com), retrieved on Apr. 30, 2009.*
Kolb et al., Nerve Growth Factor Treatment Prevents Dendritic Atrophy and Promotes Recovery of Function After Cortical Injury, Neuroscience, vol. 76, No. 4, pp. 1139-1151, (1996).
Zhang et al., "Cytoskeletal Disruption Following Contusion Injury to the Rat Spinal Cord", Journal of Neuropathology and Experimental Neurology, vol. 59, No. 4, pp. 287-296, (2000).
Schumacher et al., "Pretreatment with Calpain Inhibitor CPE-4143 Inhibits Calpain I Activation and Cytoskeletal Degradation, Improves Neurological Function, and Enhances Axonal Survival After Traumatic Spinal Cord Injury", Journal of Neurochemistry, vol. 74, No. 4, pp. 1646-1655, (2000).
Springer et al., "Rapid Calpain I Activation and Cytoskeletal Protein Degradation Following Traumatic Spinal Cord Injury: Attenuation with Riluzole Pretreatment", Journal of Neurochemistry, vol. 69, No. 4, pp. 1592-1600, (1997).
Matus, "MAP2", Microtubules, pp. 155-166, (1994).
Sánchez et al., "Phosphorylation of Microtubule-Associated Protein 2 (MAP2) and its Relevance for the Regulation of the Neuronal Cytoskeleton Function", Progress in Neurobiology, vol. 61, pp. 133-168, (2000).
Caceres, et al., "Suppression of MAP2 in Cultured Cerebeller Macroneurons Inhibits Minor Neurite Formation", Neuron, vol. 9, pp. 607-618, (1992).
Harada et al., "MAP2 is Required for Dendrite Elongation, PKA Anchoring in Dendrites, and Proper PKA Signal Transduction", The Journal of Cell Biology, vol. 158, No. 3, pp. 541-549, (2002).
Reyna-Neyra et al., "Estradiol and Progesterone Modify Microtubule Associated Protein 2 Content in the Rat Hippocampus", Brain Research Bulletin, vol. 58, No. 6, pp. 607-612, (2002).
Nakatomi et al., "Regeneration of Hippocampal Pyramidal Neurons after Ischemic Brain Injury by Recruitment of Endogenous Neural Progenitors", Cell, vol. 110, pp. 429-441, (2002).
García-Estrada et al., "Dehydroepiandrosterone, Pregnenolone and Sex Steroids Down-Regulate Reactive Astroglia in the Male Rat Brain after a Penetrating Brain Injury", Int. J. Devl. Neuroscience, vol. 17, No. 2, pp. 145-150, (1999).
Legrand et al., "Pregnenolone Reverses the Age-Dependent Accumulation of Glial Fibrillary Acidic Protein within Astrocytes of Specific Regions of the Rat Brain", Brain Research, vol. 802, pp. 125-132, (1998).
Guth et al., "Key Role for Pregnenolone in Combination Therapy that Promotes Recovery after Spinal Cord Injury", Proc. Natl. Acad. Sci. USA, vol. 91, pp. 12308-12311, (1994).
Gursoy et al., "Pregnenolone Protects Mouse Hippocampal (HT-22) Cells Against Glutamate and Amyloid Beta Protein Toxicity", Neurochemical Research, vol. 26, No. 1, pp. 15-21, (2001).
Murakami et al., "Pregnenolone Binds to Microtubule-Associated Protein 2 and Stimulates Microtubule Assembly", PNAS, vol. 97, No. 7, pp. 3579-3584, (2000).

* cited by examiner

*Primary Examiner* — Johann Richter
*Assistant Examiner* — Mei-Ping Chui
(74) *Attorney, Agent, or Firm* — Finnegan, Henderson, Farabow, Garrett & Dunner LLP (57) ABSTRACT

The invention relates to a novel use of derivatives of neurosteroids, particularly pregnenolone, for the treatment of acute or chronic lesions of the nervous system, especially certain neurodegenerative diseases, related in particular to the ability thereof to stabilize and/or increase the polymerization of neuronal microtubules.

5 Claims, 7 Drawing Sheets

NGF

NGF + Preg

NGF + 43B

USE OF 3-METHOXY-PREGNENOLONE IN THE PRODUCTION OF A MEDICAMENT FOR TREATING NEURODEGENERATIVE DISEASES

The invention involves a novel use of neurosteroid derivatives, notably pregnenolone, to treat acute or chronic nervous system lesions, in particular certain neurodegenerative diseases, notably linked to the ability of the aforementioned neurosteroid derivatives to stabilize and/or increase the polymerization of neuronal microtubules.

A deterioration of neuronal cytoskeleton is observed in the majority of CNS lesions and neurodegenerative diseases. This deterioration can be the consequence but also the cause of damage to the affected cells. Indeed, microtubule depolymerization can be directly responsible for the dysfunction of certain neurons and can result in their death. Moreover, this deterioration affects the number and the length of the neuritic extensions of the remaining neuronal cells and, as a consequence, decreases their effectiveness. Treatment with NGF, which prevents dendritic atrophy, enables better functional recovery after a lesion of the cerebral cortex in the rat (Kolb et al., Neuroscience 1996). The degradation of the cytoskeleton observed after trauma to the CNS (Zhang et al., J Neuropathol Exp Neurol 2000) or an episode of ischemia, results from many factors, in particular the increase in glutamate and intracellular $Ca^{++}$, which involves microtubule depolymerization, and in the activation of proteases such as calpain which degrade MPA2. The use of a calpain inhibiter (Schumacher et al., *J. Neurochem* 2000) and the salting-out of glutamate (Springer et al., *J Neurochem* 1997) make it possible to decrease the consequences of spinal cord trauma in the animal by partially preserving the cytoskeleton.

Lesion repair recapitulates development. The existence of stem cells in certain regions of the central nervous system is well established today. Lesions stimulate the proliferation of these cells. However, these cells must migrate and differentiate. Differentiation implies, at a fundamental level, the development of the cytoskeleton.

MAP2 proteins represent one of the major components of the proteins associated with neuronal microtubules. They are present in all the extensions which constitute the dendritic arborization of a neuron, an arborization whose importance for the establishment of synaptic connections is known (Matus, Microtubules 1994; Sanchez et al., *Prog. Neurobiol* 2000). MAP2 proteins are absolutely necessary for the formation of dendrites as has been demonstrated in work by the authors who, by the suppression of MAP2 synthesis caused either neuritic growth to stop in neurons in culture (Caceres et al., *Neuron* 1992) or dendritic growth to stop in MAP2 knockout mice (Harada et al., *J. Cell. Biol.* 2002). The synthesis of MAP2 proteins is not in and of itself sufficient to induce this dendritic growth process. Certain steroids such as estradiol or progesterone can induce an increase in MAP2 synthesis (Reyna-Neyra et al., *Brain Res.* 2002) without inducing spectacular morphological changes. On the other hand, certain molecules bound to MAP2 have the extremely important and original property of reinforcing the activity of this protein, namely its role in the activation of the tubulin polymerization process (Murakami et al., *Proc Natl Acad Sci USA* 2000) and the establishment of microtubular structures of greater stability.

It has been shown recently that, after cerebral ischemia, stem cells could differentiate into neurons and become integrated with the existing neuronal circuits (Nakatomi et al., *Cell* 2002). The stimulation of neurite growth in these cells by molecules that improve tubulin polymerization could increase their functionality.

In spite of much research, at present no specific targets other than MAPs have been identified for pregnenolone.

MAP2 protein is found primarily in neurons. The molecules bound to MAP2 thus have as a target the cells of the nervous system. It is probable therefore that they do not have a notable action on other cellular types in which the concentration of MAP2 is very low.

Studies that demonstrate an effect by pregnenolone (PREG) in vivo are very few but they suggest a beneficial role for this steroid. It was shown that PREG decreased the astrocyte reaction following a cerebral lesion (Garcia-Estrada et al., *Int J Devl Neuroscience* 1999) and in the case of the increased astrocyte size observed during ageing (Legrand and Alonso, *Brain Res.* 1998). It also contributed to improved functional recovery after a spinal cord trauma (Guth et al., *Proc Natl Acad Sci USA* 1994). PREG protects cells arising from a hippocampal line (HT-22) against toxicity induced by glutamate and the protein beta amyloid (Gursoy et al., *Neurochem Res.* 2001).

PREG is the precursor of all steroid hormones. Their synthesis implies the conversion of the PREG structure Δ5-3β-OH to Δ4-3-keto (implemented by an enzyme called 3βHSD). The Applicant blocked the Δ5-3β-OH structure to prevent its metabolism and also to prevent the formation of the ester sulfate of PREG, a molecule that can be neurotoxic at high concentrations. Thus, the Applicant has revealed a compound, 3-methoxy-pregnenolone (3β-methoxy-pregna-5-ene-20-one, abbreviated as 3β-methoxy-PREG), which possesses this property and which, moreover, is at least as active as PREG. The metabolic stability of this compound has been verified by mass spectrometry coupled with gas chromatography.

The Applicant considers as well that the invention is related to 3β-methoxy-PREG, but also to all the molecules derived from pregnenolone that contain a 3-methoxy function or present a 3' function that can be converted into 3β-methoxy-PREG. These molecules are incapable then of being converted into metabolites endowed with progestative (progesterone is a direct metabolite of PREG and, in addition to its hormonal activity, it is a PREG antagonist for the polymerization of microtubules), androgenic, estrogenic, and glucocorticoid activity. Also, they cannot be converted into ester sulfates which, like the sulfate of PREG, can have neurotoxic effects.

Within the scope of this invention, the Applicant has revealed the fact that 3β-methoxy-PREG, or other molecules according to the invention, can play a major role in the polymerization and/or stabilization of microtubules, and presents quite remarkable activities for the treatment of pathologies related to the nervous system.

By "pathologies related to the nervous system" it is meant pathologies related to the central or peripheral nervous system, particularly those pathologies in which neurocellular microtubules are affected.

3β-methoxy-PREG presents the following formula:

Thus, the invention relates to the use of 3β-methoxy-PREG or a molecule derived from pregnenolone that contains a 3-methoxy function and is incapable of being converted into a metabolite or ester sulfate of pregnenolone, for the preparation of a drug intended to stimulate the polymerization and/or the stabilization of microtubules to treat an acute or chronic lesion or a degenerative disease of the nervous system, with the aforementioned molecule presenting general formula I:

in which:

R1=—CO—; —CH(OH)— or —CH(O—COCH$_3$)—
R2=H or CHCl$_2$,
R3=H or CH$_3$, or
R2 and R3 together form a ring:

In a preferred embodiment, the aforementioned molecule is 3β-methoxy-PREG (3β-methoxy-pregna-5-ene-20-one).

In another embodiment, the aforementioned molecule is 3β-methoxy-pregna-5-ene-20-one-17-α-dichloromethyl.

In another embodiment, the aforementioned molecule is 3β-methoxy-5α-pregnane-20-one.

In another embodiment, the aforementioned molecule is 3β-methoxy-5α-pregnane-20β-ol.

In another embodiment, the aforementioned molecule is 3β-methoxy-PREG-16α-methyl.

In another embodiment, the aforementioned molecule is 3β-methoxy-PREG-16β-methyl.

In another embodiment, the aforementioned molecule is 3β-methoxy-pregna-5,14-diene-20-one.

In another embodiment, the aforementioned molecule is 3β-methoxy-PREG-16α,17α-epoxy.

In another embodiment, the aforementioned molecule is 3β-methoxy-PREG-16α,17α-methylene.

In another embodiment, the aforementioned molecule is 3β-methoxy-pregna-5-ene-3β,20β-diol-20-acetate.

In another embodiment, the aforementioned molecule is 3β-methoxy-5α-pregnane-20-one-16α-methyl.

3β-methoxy-PREG can, within the scope of the present invention, be used to prepare a useful drug to treat other syndromes such as mental slowdown and loss of concentration, pain, including acute pain, post-operative pain, chronic pain, nociceptive pain, neuropathic pain, psychogenic pain syndromes, pain associated with peripheral neuropathies, certain psychiatric states (notably depressive states), dissociative episodes including dissociative amnesia, dissociative fugue and dissociative identity disorder, and other neurodegenerative diseases such as Parkinson's disease, Huntington's disease, diseases related to prions, amyotrophic lateral sclerosis (ALS), and multiple sclerosis.

In a general way, 3β-methoxy-PREG or the molecule derived according to the invention is used to treat any disease in which increased microtubule polymerization and/or stabilization is sought or is beneficial.

In a preferred embodiment according to the invention, the aforementioned disease is selected from the group comprising Alzheimer's disease, Parkinson's disease, age-induced memory loss, memory loss induced by the taking of substances, a traumatic lesion, a cerebral lesion, a lesion of the spinal cord, in particular spinal cord compression, ischemia, pain, notably neuralgia, nerve degeneration, and multiple sclerosis.

In a preferred embodiment, and notably to treat diseases related to a central nervous system disturbance, the aforementioned drug also comprises an excipient or a compound that makes it possible to formulate the aforementioned 3β-methoxy-PREG such that it crosses the blood-brain barrier better. Such an excipient or compound can also make possible a faster or more long-lasting crossing of the aforesaid blood-brain barrier.

Such an excipient or compound can be a peptide, such as the peptides described in application WO 00/32236, or 2-pyrrolidone.

The pharmaceutical compositions used in the invention can be administered by any route of administration including, but not being limited to, oral, intravenous, intramuscular, intraarterial, intraspinal, intraventricular, transdermal, subcutaneous, intraperitoneal, intranasal, enteral, topical, sublingual, and rectal.

A continuous or long-term treatment conducted directly via the cerebrospinal fluid using a pump implanted in the subarachnoid space in the brain or spinal cord can be envisaged. Such an implant could contain a concentrated solution of 3β-methoxy-PREG (for example of isopropyl-beta-cyclodextrin diluted with artificial cephalorachidian fluid).

Moreover, 3β-methoxy-PREG can be administered with other compounds that contain biologically active agents (for example tensioactives, excipients, transporters, thinners and/or pharmaceutically acceptable vehicles). These compounds are well-known to those skilled in the art. Details on these chemicals can be found in the latest edition of Remington's Pharmaceutical Sciences (Maack Publishing Co., Easton, Pa.).

In the pharmaceutical compositions provided by the present invention for oral, sublingual, subcutaneous, intramuscular, intravenous, transdermal, local, or rectal administration, the active ingredient 3β-methoxy-PREG or a derived molecule) can be administered in unit dose formulations or in mixtures with traditional pharmaceutical media, applicable to animals or humans. Suitable unit dose administration formulations include oral route formulations such as tablets, coated tablets, pills, capsules and soft gelatin capsules, oral powders, granules, solutions and suspensions, sublingual and buccal administration formulations, subcutaneous, intramuscular, intravenous, intranasal, and intraocular administration formulations, and rectal administration formulations.

Pharmaceutical compositions can also contain preservatives, solubilizing agents, stabilizers, wetting agents, emulsifiers, sweeteners, dyes, flavoring, salts intended to modify osmotic pressure, buffers, taste correctors, and antioxidants. They can also contain other therapeutically active substances.

Thus, pharmaceutical compositions according to the invention can also contain other neuroprotective agents, notably compounds which increase neuronal regeneration. Such agents can be selected in particular from among the neuronal growth factors such as fibroblast growth factors (FGFs), acidic or basic, FGF-3, FGF-4, FGF-6, or keratinocyte growth factor (KGF). The addition of a neuroprotective agent can be envisaged, such as nerve growth factor (NGF), brain derived neurotrophic factor (BDNF), neurotrophin 3 or 4, TGF-beta.1, interleukins, or insulin-like growth factors (IGFs).

Any other types of therapeutic antioxidant or neuroprotective agents can be used, notably glutamate inhibitors.

When a solid composition in tablet form is prepared, the principal active ingredient is mixed with a pharmaceutical vehicle such as gelatin, starch, lactose, stearic acid or magnesium stearate, talc, gum arabic or analogues. The tablets can be coated with saccharose or other suitable materials or even be treated so as to have a prolonged or delayed activity and to release continuously a predetermined quantity of the active ingredient.

A capsule preparation is obtained by mixing the active ingredient with a thinner and pouring the mixture obtained into soft or hard capsules, with excipients such as vegetable oils, waxes, fats, semi-solid or liquid polyols, etc.

A preparation in syrup or elixir form can contain the active ingredient together with a sweetener, an antiseptic, as well as an agent giving taste and a suitable dye. Excipients can be used such as water, polyols, saccharose, invert sugar, glucose, etc.

Powders or water-dispersible granules can contain the active ingredient in a mixture with dispersing agents, wetting agents, and suspending agents, just as with taste correctors and sweeteners.

Suppositories, which are prepared with binders that melt at rectal temperatures, for example cocoa butter or semi-solid or liquid polyols such as polyethylene glycols, waxes, natural or hydrogenated oils, fats, etc., can be used for rectal administration.

For parenteral, intranasal, or intraocular administration, aqueous suspensions, isotonic saline solutions, or sterile, injectable solutions that contain pharmacologically compatible dispersing agents and/or wetting agents can be used. As an excipient, water, alcohols, polyols, glycerol, vegetable oils, etc., can be used.

The active ingredient can also be formulated in the form of microcapsules, possibly with one or more additive supports.

For the treatment of pain, topical application is the preferred route of administration. Here, the compositions according to the invention can be presented in the form of a gel, a paste, an ointment, a cream, a lotion, an aqueous or aqueous-alcohol liquid suspension, an oily solution, a dispersion of the lotion or serum type, an anhydrous or lipophilic gel, an emulsion with a liquid or semi-solid milk-type consistency obtained by dispersing a fatty phase in an aqueous phase or vice versa, suspensions or emulsions of a soft or semi-solid cream- or gel-type consistency, or alternatively microemulsions, microcapsules, microparticles, or vesicular dispersions of the ionic and/or nonionic type. These compositions are prepared according to standard methods.

Moreover, a tensioactive can be included in the composition in order to enable deeper penetration by 3β-methoxy-PREG.

Among the ingredients envisaged, the invention comprises agents enabling an increase in penetration selected, for example, from the group comprising mineral oil, ethanol, triacetin, glycerin and propylene glycol; cohesion agents are selected, for example, from the group comprising polyisobutylene, polyvinyl acetate, polyvinyl alcohol, and thickening agents.

Thus, in a preferred embodiment according to the invention, the aforementioned drug is presented in an injectable form.

In another preferred embodiment according to the invention, the aforementioned drug is presented in a form allowing oral administration.

Preferably, the aforementioned drug comprises an effective quantity of 3β-methoxy-PREG, in particular ranging between 50 and 2500 mg by the parenteral route.

The aforementioned drug comprises preferentially an effective quantity of 3β-methoxy-PREG or a molecule derived from pregnenolone that presents a 3-methoxy function, such that the quantity administered to the patient is comprised between 1 and 100 mg/kg.

An effective quantity of 3β-methoxy-PREG is a quantity which allows, within the meaning of the present invention, the stabilization and/or polymerization of microtubules after administration to the host. Thus, the administration of an effective quantity of 3β-methoxy-PREG results in the improvement or the elimination of the disease. The quantity of 3β-methoxy-PREG administered to the host will vary as a function of factors which include the height, age, weight, general health, sex, and diet of the host, the time of the administration, and the duration and characteristics of the disease associated with microtubule depolymerization/destabilization. For example, the dosage must reach, at the site of action, a concentration on the order of 0.5 to 100 µM. The adjustment of dosages is well-known to those skilled in the art.

Thus, the invention relates to a therapeutic use of 3β-methoxy-PREG. Thus, the invention relates to this compound as a drug.

A pharmaceutical composition comprising as an active ingredient 3β-methoxy-PREG or a compound derived from pregnenolone having a 3-methoxy function of general formula I, and a pharmaceutically acceptable excipient, is also an object of the invention.

The Applicant has revealed the activity of 3β-methoxy-PREG which stabilizes and/or induces microtubule polymerization in a cell.

Thus, in a more general way, the invention relates to a method for increasing the stabilization and/or inducing the polymerization of the microtubules in a cell, comprising the step of exposing the aforementioned cell to the presence of 3β-methoxy-PREG at a concentration from approximately 0.5 to 100 µM, preferably 0.5 to 50 µM. Microtubule polymerization can be indicated and marked by immunolabeling the MAP2 protein associated with these microtubules. Preferably, this method is implemented in vitro, but can be implemented in vivo, or ex vivo (on cells isolated from a patient, treated in vitro and reinjected) in certain cases.

The invention also relates to a method for increasing the growth of neurites in a cell, comprising the step of exposing the aforementioned cell to the presence of 3β-methoxy-PREG at a concentration from approximately 0.5 to 50 µM. This method is also recommended in vitro by preference, without excluding other modes of implementation if necessary.

The invention has also as an aim a method for reducing the depolymerization of microtubules and/or the retraction of neurites in a cell, comprising the step of exposing the aforementioned cell to the presence of 3β-methoxy-PREG at a concentration from approximately 0.5 to 50 μM. This method is implemented in vitro also by preference, without excluding other modes of implementation if necessary.

The invention also relates to a method for the treatment and/or the prevention of a disease induced or accompanied by the depolymerization of microtubules in a patient, comprising the step of the administration of an effective quantity of 3β-methoxy-PREG to the aforementioned patient, or to a method for the treatment and/or the prevention of a neurodegenerative disease or lesion in a patient, comprising the step of the administration of an effective quantity of 3β-methoxy-PREG to the aforementioned patient.

Finally, a method to treat a patient after spinal cord compression or trauma, comprising the step of the administration of an effective quantity of 3β-methoxy-PREG to the aforementioned patient, is also an object of the invention.

The examples which follow are intended to illustrate the invention.

EXAMPLES

Example 1

Synthesis of 3-methoxy-PREG 10 g (52 mmol) of p-toluenesulfonyl chloride is added to a solution of 5 g (15.8 mmol) of pregnenolone in 30 ml of pyridine. The mixture is stirred for 14 hours and then added to 100 ml of distilled water. After cooling the reaction medium to 0° C., the mixture is filtered and the white solid obtained is dried under vacuum to yield 7.4 g (98%) of pregnenolone tosylate.

The 7.4 g of pregnenolone tosylate is refluxed with methanol (50 ml) for 4 hours. After cooling and evaporation of the solvent, the crude reaction product is taken up in 100 ml of ethyl and washed 3 times with 100 ml of a 10% sodium bicarbonate solution. After drying the organic phase over $Na_2SO_4$, it is evaporated dry under reduced pressure to yield 5.2 g (100%) of 3β-methoxy-PREG in the form of a white powder.

A novel synthesis of 3β-methoxy-PREG was performed on a kilogram scale. The purity of the end product was confirmed by NMR and was greater than 97.5%, with only one minor contaminant easily separable by HPLC. Pregnenolone can be obtained at low cost from commercial sources.

Example 2

Test of 3-methoxy-PREG Activity; Comparison with PREG

Figure 1:
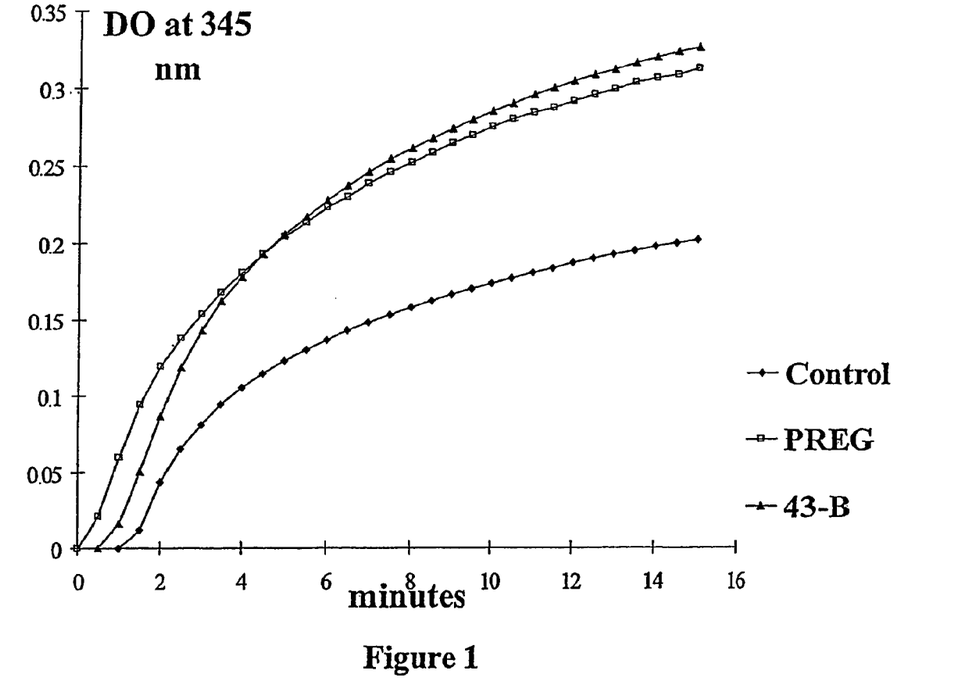
FIG. 1: Kinetics of microtubule polymerization in vitro: effects of PREG (pregnenolone) and molecule 43B (3β-methoxy-PREG). Purified MAP2 and tubulin are mixed in the presence of GTP at 4° C. in a spectrophotometer cuvette. Polymerization is induced by heating at 37° C. and is followed by the increase in optical density (OD) which indicates the quantity of polymers formed. Lag time is decreased in the presence of PREG and molecule 43B, whereas the polymerization rate and the quantity of microtubules clearly increase compared to the control kinetics in the presence of solvent alone.

This in vitro test measures the effect of molecules on the polymerization of MAP2-induced microtubules. This polymerization occurs when MAP2 proteins and tubulin are mixed at adequate concentrations in the presence of GTP. It is accompanied by an increase in optical density measured at 345 nm for 15 to 30 minutes with a UNICON spectrophotometer thermostated at 37° C. (FIG. 1).

It is observed that molecule 43B, corresponding to 3β-methoxy-PREG, activates microtubule polymerization as does pregnenolone (PREG). Other molecules, such as progesterone and pregnenolone sulfate, are PREG antagonists and do not stimulate polymerization (not shown).

Example 3

Cellular Models

Effect of Molecules on Neurite Outgrowth

Figure 2:
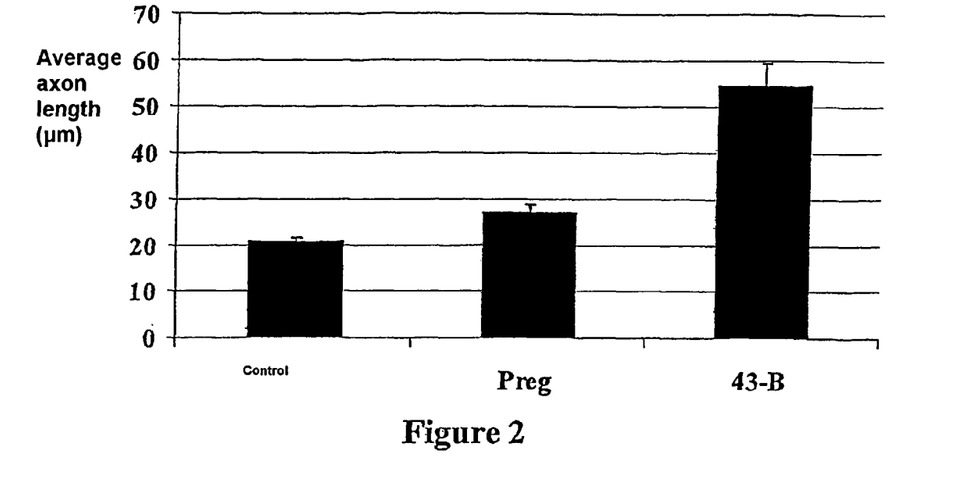
FIG. 2: Effect of PREG and 3β-methoxy-PREG (43B) on the average length of neurites in PC12 cells. PC12 cells were cultured for 3 days in the presence of NGF (10 ng/ml) with or without (control) the addition of PREG or 43B molecules (30 μM). Each molecule was tested in three culture wells. Measurements were taken for 200 cells per well using Scion Image software. Measurements were taken for 200 cells per well using Scion Image software.
Figure 3:
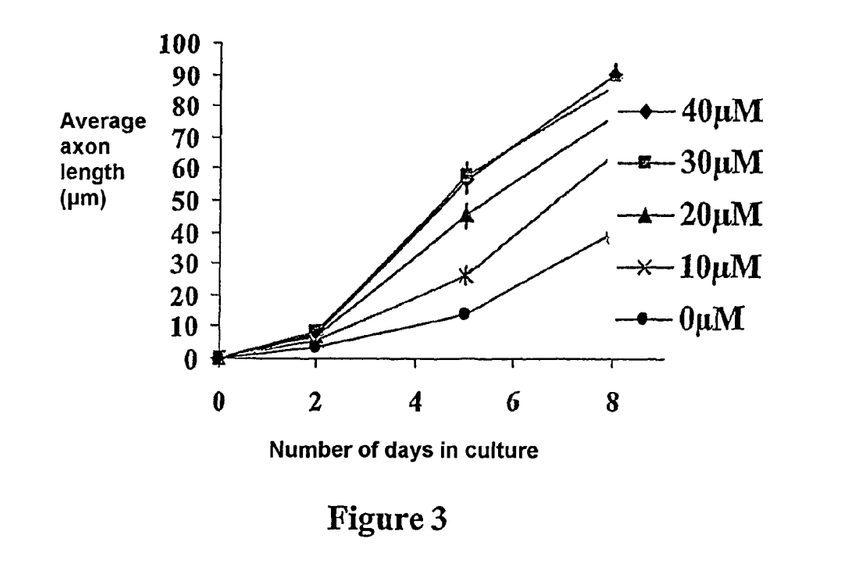
FIG. 3: Dose-response relationship of molecule 43B on the average length of neurites in PC12 cells. PC12 cells were cultured in the presence of NGF (10 ng/ml) and increasing concentrations of 3β-methoxy-PREG (43B). Neurite length was measured for 200 cells per well after 2, 5, and 8 days of culture.
Figure 4:
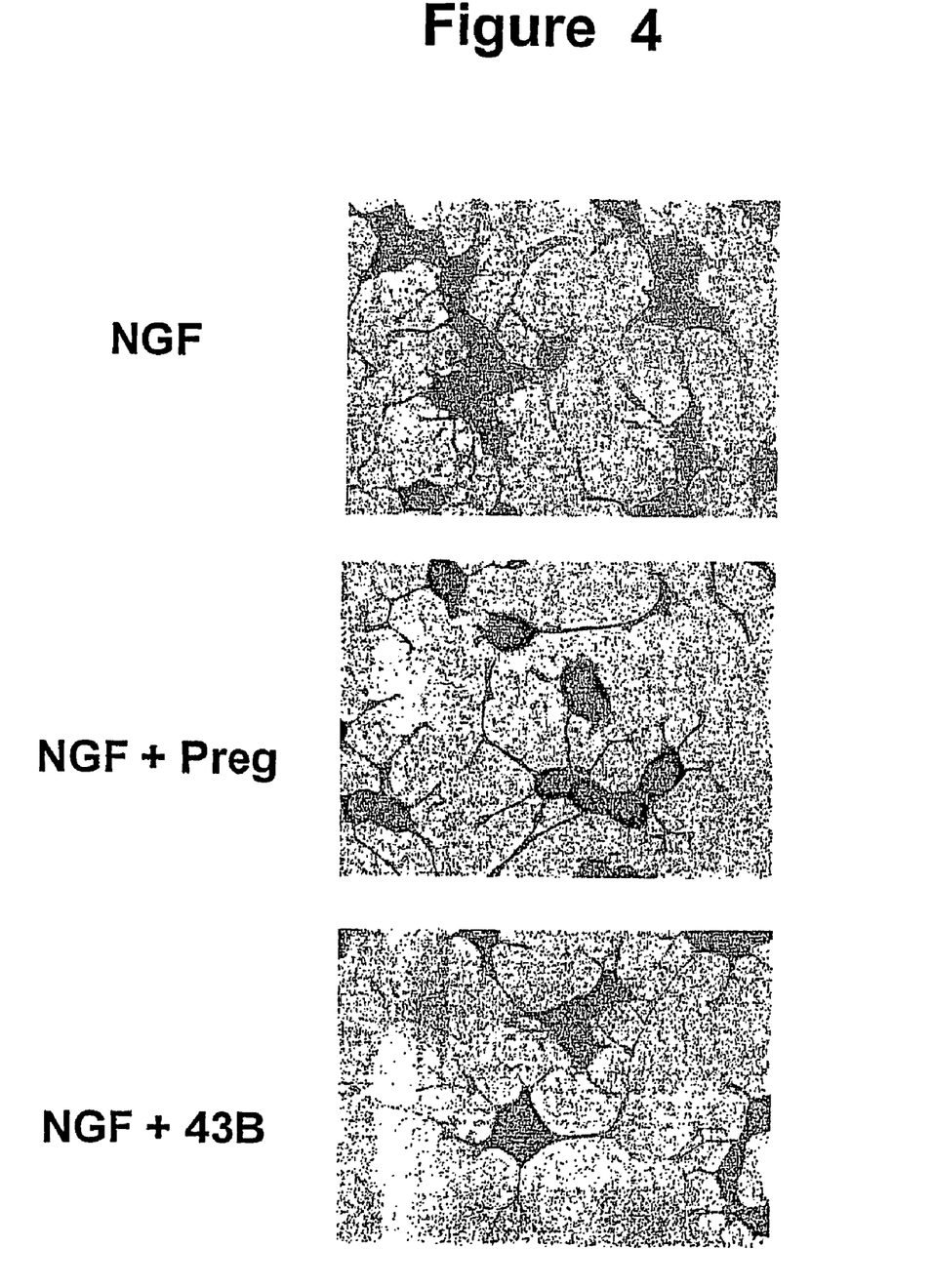
FIG. 4: Immunolabeling of microtubule-associated MAP2 in PC12 cells treated with PREG or 3β-methoxy-PREG. PC12 cells were cultured in the presence of NGF (10 ng/ml) and PREG or 3β-methoxy-PREG (20 μM). They are fixed and exposed to anti-MAP2 antibodies that reveal microtubule-associated MAP2 exclusively.

To test the effect of selected molecules on neurite outgrowth, we first used the PC12 lines, which has long been employed in neurobiological research. In the presence of NGF (nerve growth factor), the cells of this line, which arise from a rat pheochromocytoma, form neuritic extensions containing MAP-associated microtubules. The growth of these elongations is stimulated by the addition of PREG. In the presence of PREG (30 µM), the increase in the average length of the neurites after 4 days of culture reaches 60%. The screening of other natural or synthetic steroids made it possible to select several molecules presenting greater effects than that of PREG (FIG. 2). In particular, the addition of molecule 43B, which can be synthesized easily from PREG, caused a spectacular increase (reaching as high as 500%) in the length of neurites formed in the presence of NGF (FIG. 3). This neurite growth accompanies the estimation by 43-B of the association of MAP to the microtubules (FIG. 4).

Effect of Steroids on the Resistance of Microtubules to Nocodazole

Figure 5:
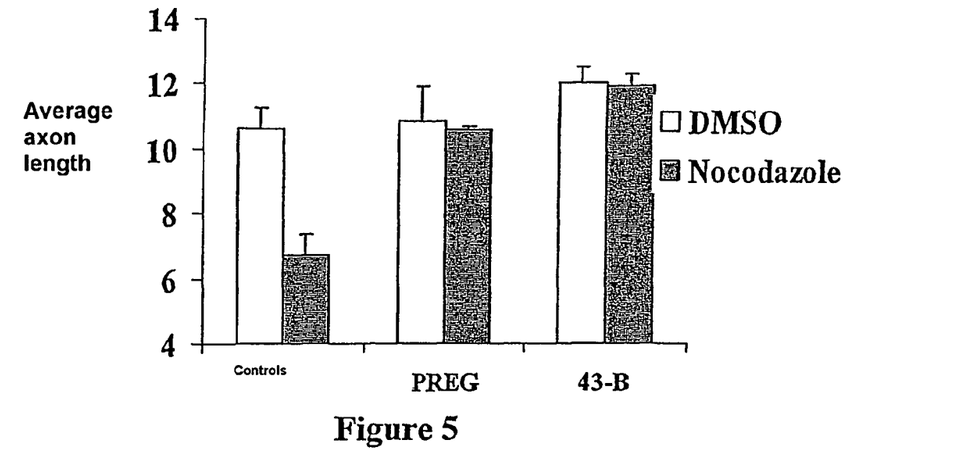
FIG. 5: Retraction of neurites induced by nocodazole. After 7 days of culture in the presence of NGF (10 ng/ml), the cells were pretreated for one hour with PREG (30 μM) or 43B (30 μM), then exposed to nocodazole for 15 minutes (white columns: DMSO solvent alone; gray columns: nocodazole).

Nocodazole is a microtubule depolymerizing agent. Its addition to PC12 cell cultures, differentiated in the presence of NGF, causes neurites to retract as a result of the depolymerization of their microtubules. Pretreatment of the cells by PREG or 43B makes the neurites resistant to nocodazole due to an increase in the stability of their microtubules, a condition necessary for the formation of long neurites (FIG. 5).

Effect of Steroids on the Cytotoxicity of Okadaic Acid

Figure 6:
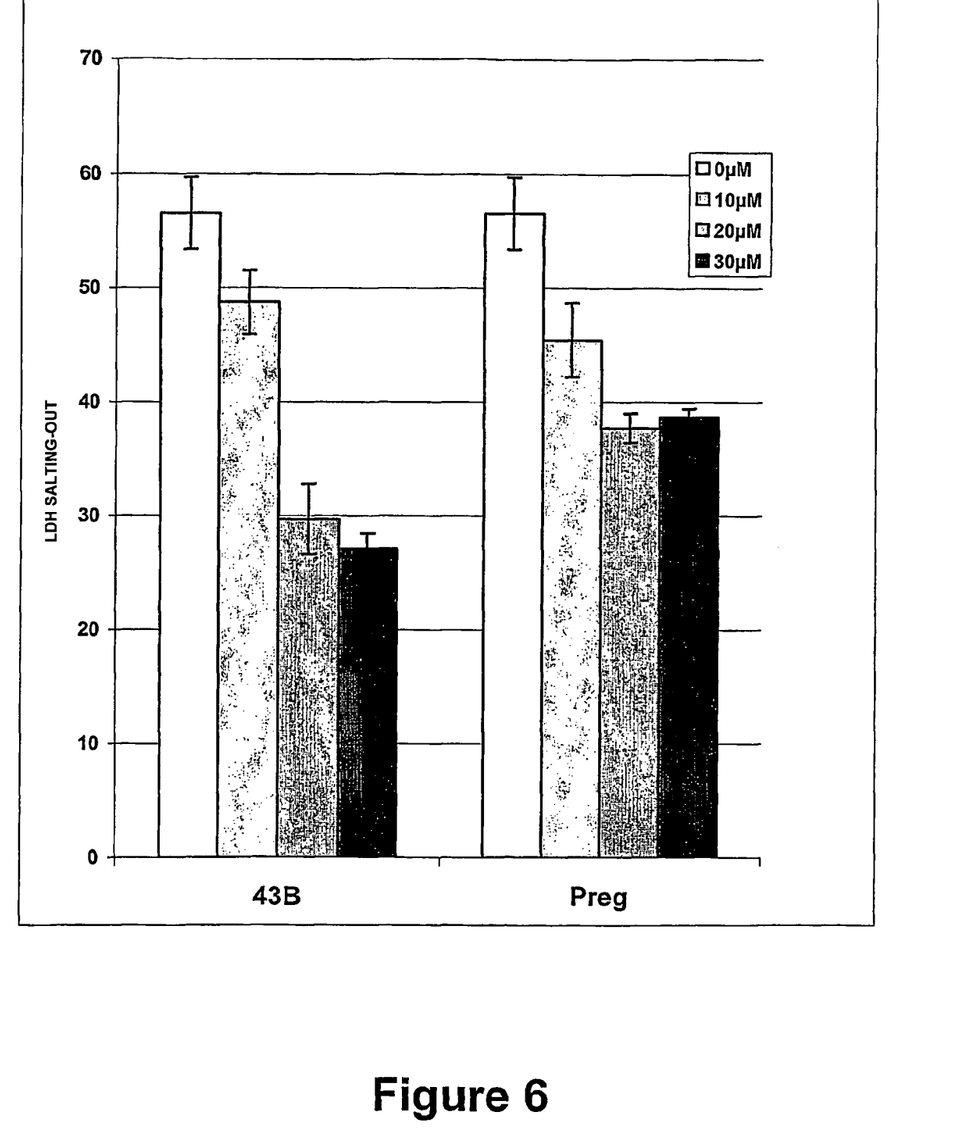
FIG. 6: Toxicity of okadaic acid. Steroid protection. Human neuroblastoma HS-SY5Y cells were cultured for 24 hours in the presence of okadaic acid only or associated with increasing concentrations of PREG or 3β-methoxy-PREG. Cell death was indicated by the release of lactate dehydrogenase (LDH) in the culture medium.

Okadaic acid is a protein phosphatase inhibiter. Thus, the hyperphosphorylation of tau protein is implicated in microtubule depolymerization and in human neuroblastoma HS-SY5Y cell death. The exposure of SY5Y cell cultures to okadaic acid does in fact cause significant cell death. Cell death is decreased by the simultaneous addition of PREG and the same effect, only much stronger, is seen by the simultaneous addition of 3β-methoxy-PREG (43B) (FIG. 6).

Example 4

Tests of Toxicity

Cellular Toxicity

Cellular toxicity tests are carried out routinely on the PC12 cell line. The initial results show that PREG and 43B do not demonstrate toxicity at concentrations as high as their solubility limits (approximately 50 µM).

In Vivo Toxicity

In rats, the daily injection for one month of 48 mg/kg of 43B (which is 4 times the active dose for spinal cord trauma) affected neither average weight nor behavior.

Example 5

In Vivo Experiments—Spinal Cord Trauma

Spinal Cord Contusion Model

To determine the neuroprotective effects of the molecules tested, a spinal cord compression model is used. This model involves the total paralysis of the animals in the first few days following the operation. This period of paralysis is followed of a phase of approximately three weeks during which the animals partially recover their motor function. The study of this recovery using a simple and precise functional test based on observation of the animals (the BBB score) makes it possible to study the speed and the degree of recovery of the animals, with and without treatment.

Figure 7:
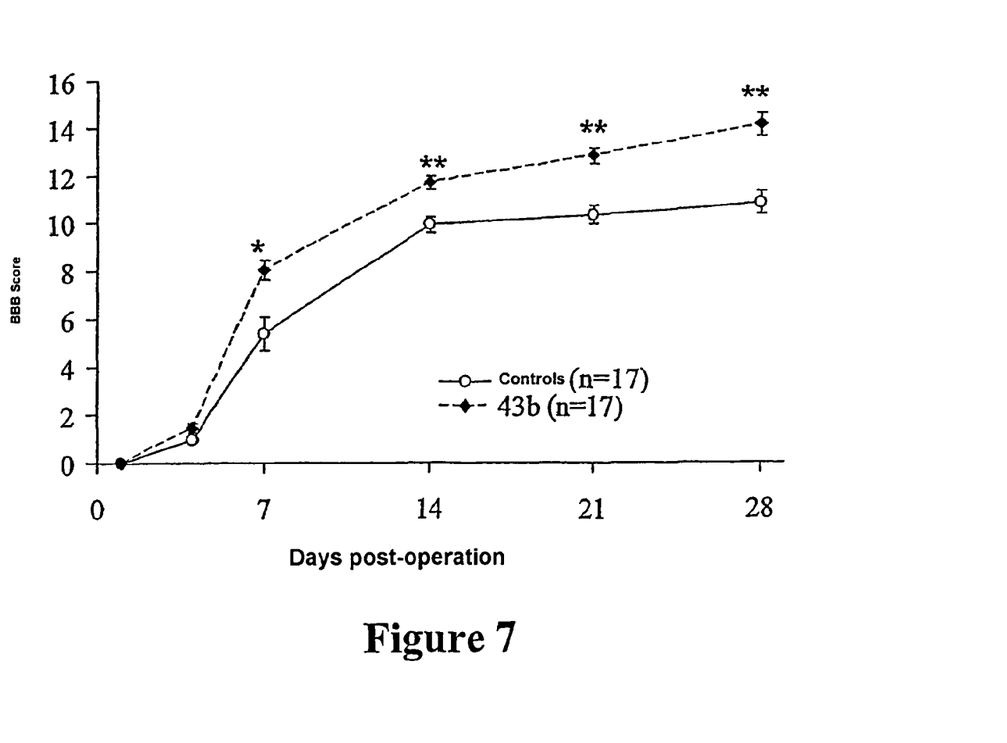
FIG. 7: Effect of molecule 43B on locomotor recovery following spinal cord compression in rats. Animal locomotion was evaluated in a blind format during the 1-28 day post-operative period using the BBB score which evaluates the degree of paralysis (higher values correspond to better recovery). Statistical significance: * indicates $p<0.001$; ** indicates $p<0.0001$.

Two groups of rats were subjected to spinal cord compression. Then, daily for 2 weeks, the animals received a subcutaneous injection containing either sesame oil alone (control group, n=20), or sesame oil containing molecule 43B (43B group, n=20; 12 mg/kg/day). The first injection was given 5 minutes after spinal cord compression. Locomotion of the animals, using BBB scores, was evaluated in a blind format on post-operation days 1, 4, 7, 14, 21, and 28. Three animals in each group had to be excluded from the study. Statistical analysis of the results using the nonparametric Mann-Whitney test shows that the animals treated with 43B present results quite significantly higher than the control animals as of post-operation day 7 (FIG. 7).

Example 6

In Vivo Experiments—Cerebral Ischemia

Two models of cerebral ischemia in the rat were developed.

The first is a permanent or transient focal ischemia model of the middle cerebral artery using electrocoagulation or clamping (evaluation of neuroprotection by quantification of the volume of the lesioned area).

The second is a transient global cerebral ischemia model. This model is created in the rat by electrocoagulating and severing the vertebral arteries and then clamping the carotid arteries for a period of 15 minutes (evaluation of neuroprotection and cerebral plasticity increase by quantification of neuronal loss in the CA1 region of the hippocampus and by memory tests).

Example 7

In Vivo Experiments—Alzheimer-Type Neurodegenerative Disease Model (Transgenic Mice)

In order to evaluate the therapeutic potential of 43B to treat Alzheimer-type neurodegenerative diseases, a homozygous transgenic line of mice, such as described by Götz (EMBO J. 1995; 14(7):1304-13), can be used.

These mice express the longest human tau protein isoform. They present symptoms of neurological dysfunction expressed as muscular weakness and a reduction in motor coordination which correlate histologically with the appearance of abnormal neurites and hyperphosphorylated tau proteins as is seen in Alzheimer's disease. This pathological phosphorylation decreases the affinity of tau for microtubules and favors its aggregation.

By treating these mice with molecules that increase microtubule stability, it is intended that the proportion of tau protein associated with the microtubules is increased and thus the appearance of symptoms is delayed.

Figure 8:
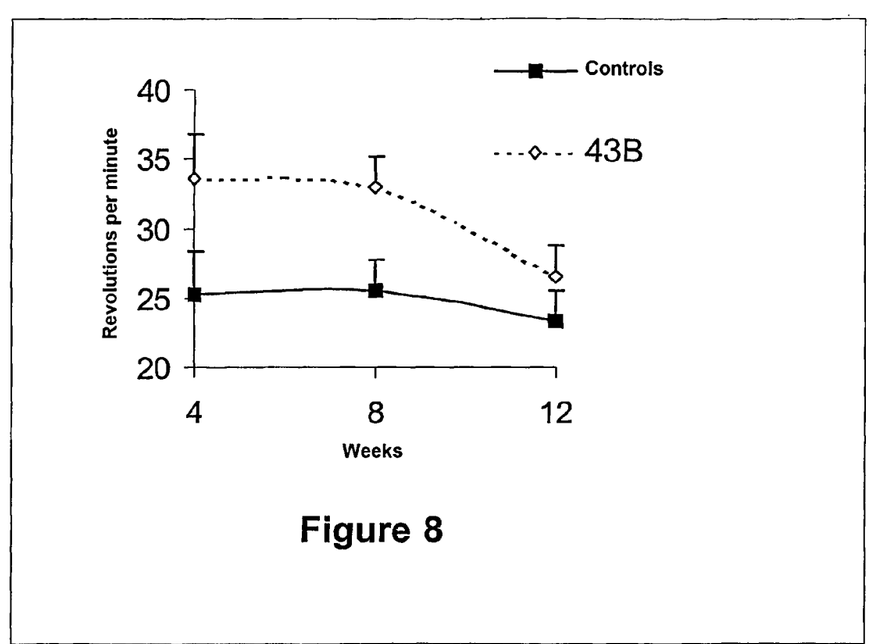
FIG. 8: Effect of molecule 43B on the motor incoordination of transgenic mice expressing the longest isoform of human tau protein in their neurons. Motor incoordination was evaluated in a blind format during 12 weeks following subcutaneous insertion of an implant that was empty or contained either PREG or 3β-methoxy-PREG (43B). The maximum speed of rotation of the RotaRod drum before the rat falls is a measurement of motor coordination (higher values correspond to a better treatment effect).

A breeding program was undertaken at Bicêtre and genotyping made it possible to select mice homozygous for the transgene. At the age of 21±3 days, 3 groups of 10 mice were assembled and each group then received subcutaneously either an empty implant, an implant of PREG, or an implant of 3β-methoxy-PREG. These implants released 0.38 mg of steroid per day for 90 days. The progression of motor incoordination was followed by repeated RotaRod tests. Only the 3β-methoxy-PREG had a beneficial effect on motor dysfunction (FIG. 8).

Example 8

In Vivo Experiments—Mnemonic Performance

Mnemonic Deficit Induced by Colchicine

Colchicine, a substance which depolymerizes microtubules without blocking protein synthesis, is injected at very low doses that do not induce neuronal death in the rat hippocampus. These injections cause a learning deficit which results from lasting microtubule depolymerization. The objective is to test the effect of microtubule-stabilizing molecules on mnemonic deficits and histological lesions in the hippocampus induced by colchicine.

Mnemonic Deficit During Ageing

Studies on ageing are carried out on old rats presenting mnemonic deficits. The objective of this experiment is to mitigate these deficits by a chronic treatment with our molecules.

The two-step memory experiments are based on the spontaneous exploration of novelty and are adapted from the experiments described by Dellu et al. (1992, Brain Res., 588, 132-9) and Ladurelle et al. (2000, Brain Res., 858, 371-9). The technical instructions from these two publications concerning spatial memory tests using labyrinths are included in reference to the present application.

Example 9

Pharmacokinetics

The pharmacokinetics of the molecules tested in vivo are evaluated using gas chromatography/mass spectrometry (GC/MS) assays.

A study was conducted with PREG and molecule 43B. Its primary objective was to show that molecule 43B crossed the blood-brain barrier.

Rats were injected with either PREG or 43B diluted in sesame oil and assayed by GC/MS for the quantity of PREG or 43B in various organs at 1, 4, 8, and 24 hours after injection (12 mg/kg in 0.5 ml of sesame oil; subcutaneous injection).

Figure 9:
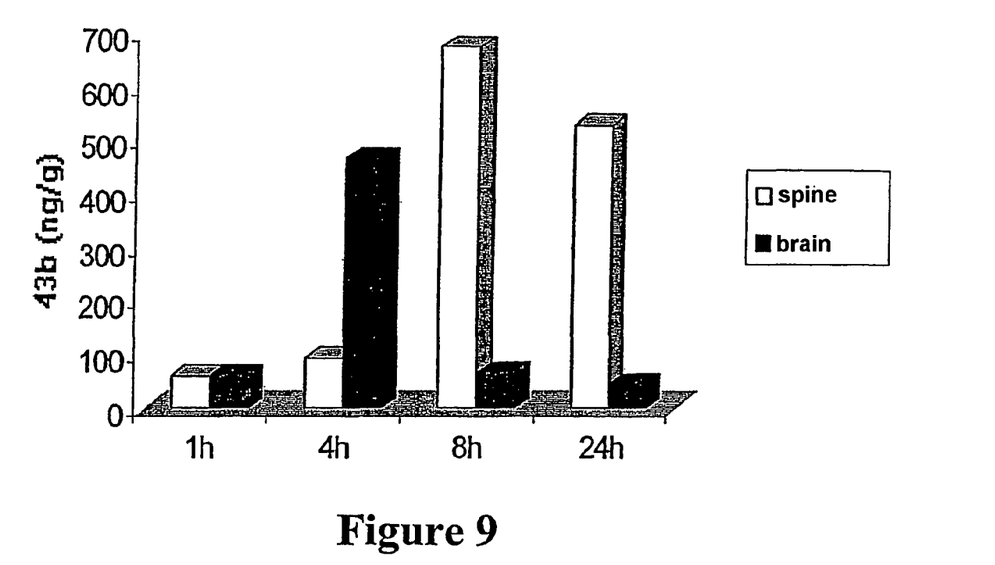
FIG. 9: Kinetics of the appearance of 3β-methoxy-PREG (43B) in rat brain and spinal cord following subcutaneous injection of 43B (12 mg/kg) in a sesame oil solution.

The results presented in FIG. 9 show that molecule 43B penetrates rapidly into the spinal cord and the brain of the injected rats, and tends to accumulate there.

These results obtained in vitro and in vivo clearly demonstrate that molecule 43B (3β-methoxy-PREG) gives spectacular results on the growth of neurites in culture and on the spinal cord compression model.

Example 10

Other Molecules According to the Invention

The indices of binding and activity are expressed as a percent of PREG.

Blending (affinity) is measured by the displacement of PREG-$^3$H.

Activity is measured by the increase in optical density at 345 nm of a mixture of purified tubulin and MAP2, incubated at 37° C. in the presence of GTP.

Stimulation of neurite outgrowth is conducted on PC12 cells differentiated in the presence of NGF (10 ng/ml) and the steroid being tested (30 μM) for 3 days. For each condition, the average length of the longest 200 neurites in each cell is measured simultaneously for 3 cultures.

The results are represented by one, two or three crosses (+) according to whether stimulation is lower than, equal to, or higher than that produced by PREG.

| Steroid | Affinity | Activity | Neurite sprouting |
|---|---|---|---|
| Pregnenolone (PREG) | 100 | 100 | ++ |
| 3β-methoxy-pregna-5-ene-20-one | 100 | 100 | +++ |
| 3β-methoxy-pregna-5-ene-20-one-17α-dichloromethyl | 53 | 113 | +++ |
| 3β-methoxy-5α-pregnane-20-one | 87 | 10 | +++ |
| 3β-methoxy-5α-pregnane-20β-ol | 65 | 65 | ++ |
| PREG-16α-methyl | 80 | 70 | ++ |
| PREG-16β-methyl | 63 | 67 | (++) |
| 3β-methoxy-pregna-5,14-diene-20-one | 102 | 50 | + |
| PREG-16α,17α-epoxy | 41 | 54 | + |
| PREG-16α,17α-methylene | 62 | 49 | + |
| Pregna-5-ene-3β,20β-diol-20-acetate | 60 | 108 | ++ |
| 3β-hydroxy-5α-pregnane-20-one-16α-methyl | 57 | 53 | (+) |

These results show the effectiveness of other molecules derived from pregnenolone to stimulate the polymerization of microtubules induced by MAP2 and to stimulate neurite sprouting. For those that are not 3β-methyl derivatives, it is foreseeable that these derivatives will at least maintain their activity.

The invention claimed is:

1. A method for treating an acute or chronic spinal cord lesion in a patient comprising administering to the patient a composition comprising 3β-methoxy-pregna-5-ene-20-one (3β-methoxy-PREG),
   wherein the composition is administered to the patient in an amount effective to treat the acute or chronic spinal cord lesion.

2. The method according to claim 1, wherein said acute or chronic spinal cord lesion is spinal cord compression.

3. The method according to claim 1, wherein said composition is administered by injection.

4. The method according to claim 1, wherein said composition is administered orally.

5. The method according to claim 1, wherein said composition comprises a quantity of 3β-methoxy-PREG ranging between 50 and 2500 mg.

\* \* \* \* \*